United States Patent
Concepcion et al.

(10) Patent No.: US 10,518,015 B2
(45) Date of Patent: Dec. 31, 2019

(54) DIALYSIS MACHINES WITH INTEGRAL SALT SOLUTION CHAMBERS AND RELATED METHODS

(71) Applicant: Fresenius Medical Care Holdings, Inc., Waltham, MA (US)

(72) Inventors: James Concepcion, Concord, CA (US); Robert E. Hassard, Benicia, CA (US); Christopher McCormick, Walnut Creek, CA (US); Roland Levin, San Ramon, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 83 days.

(21) Appl. No.: 15/784,777

(22) Filed: Oct. 16, 2017

(65) Prior Publication Data

US 2018/0036467 A1    Feb. 8, 2018

Related U.S. Application Data

(62) Division of application No. 14/739,199, filed on Jun. 15, 2015, now Pat. No. 9,814,819.

(51) Int. Cl.
*A61M 1/16* (2006.01)

(52) U.S. Cl.
CPC .......... *A61M 1/1668* (2014.02); *A61M 1/168* (2013.01); *A61M 1/1666* (2014.02);
(Continued)

(58) Field of Classification Search
None
See application file for complete search history.

(56) References Cited

U.S. PATENT DOCUMENTS

| 3,669,880 A | 6/1972 | Marantz |
| 6,524,231 B1 * | 2/2003 | Westberg ............. B04B 5/0442 494/43 |

(Continued)

FOREIGN PATENT DOCUMENTS

| DE | 9418915 | 2/1995 |
| EP | 0909187 | 9/2004 |

(Continued)

OTHER PUBLICATIONS

Notification of Transmittal of the International Search Report and the Written Opinion of the International Searching Authority for corresponding PCT Application No. PCT/US2016/034791, dated Aug. 12, 2016, 14 pages.

(Continued)

*Primary Examiner* — Krishnan S Menon
(74) *Attorney, Agent, or Firm* — Fish & Richardson P.C.

(57) ABSTRACT

A hemodialysis machine includes a main body and a door connected to the main body. The door and the main body cooperate to define a non-removable chamber. The door is openable relative to the main body of the hemodialysis machine to allow a salt to be placed into the non-removable chamber when the door is in an open position. The main body further includes a fluid inlet, a fluid outlet, and a pumping mechanism. The fluid inlet and the fluid outlet are in fluid communication with the non-removable chamber. The pumping mechanism is configured to deliver a fluid from a fluid source to the non-removable chamber through the fluid inlet to mix with salt within the non-removable chamber to form a salt solution that exits the non-removable chamber through the fluid outlet.

20 Claims, 7 Drawing Sheets

(52) U.S. Cl.
CPC ........ *A61M 1/1682* (2014.02); *A61M 1/1686* (2013.01); *A61M 2205/7545* (2013.01)

(56) References Cited

U.S. PATENT DOCUMENTS

| | | |
|---|---|---|
| 8,038,886 B2 | 10/2011 | Folden et al. |
| 2013/0037233 A1* | 2/2013 | Sato .................. B22D 11/0611 164/463 |
| 2015/0083647 A1 | 3/2015 | Meyer et al. |

FOREIGN PATENT DOCUMENTS

| | | |
|---|---|---|
| WO | 0057935 | 10/2000 |
| WO | WO 00/57935 | 10/2000 |
| WO | 2010114932 | 10/2010 |
| WO | WO 2010/114932 | 10/2010 |
| WO | 2011011215 | 2/2011 |
| WO | WO 2011/011215 | 2/2011 |
| WO | 2014052596 | 4/2014 |
| WO | WO 2014052596 | 4/2014 |
| WO | 2015003043 | 1/2015 |
| WO | WO 2015/003043 | 1/2015 |

OTHER PUBLICATIONS

International Preliminary Report on Patentability in International Application No. PCT/US2016/034791, dated Dec. 19, 2017, 9 pages.

* cited by examiner

DIALYSIS MACHINES WITH INTEGRAL SALT SOLUTION CHAMBERS AND RELATED METHODS

CROSS-REFERENCE TO RELATED APPLICATION

This application is a divisional of and claims priority under 35 U.S.C. § 121 to U.S. Ser. No. 14/739,199, filed Jun. 15, 2015, now U.S. Pat. No. 9,814,819. The contents of this priority application are hereby incorporated by reference in their entirety.

TECHNICAL FIELD

This disclosure relates to dialysis machines with integral salt solution chambers and related methods.

BACKGROUND

Renal dysfunction or failure and end-stage renal disease causes the body to lose the ability to remove water and minerals, to excrete harmful metabolites, to maintain acid-base balance, and to control electrolyte and mineral concentrations within physiological ranges. Toxic uremic waste metabolites, including urea, creatinine, and uric acid, accumulate in the body's tissues which can result in a person's death if the filtration function of the kidney is not replaced.

Dialysis is commonly used to replace kidney function by removing these waste toxins and excess water. In one type of dialysis treatment—hemodialysis—toxins are filtered from a patient's blood externally in a hemodialysis machine. Blood passes from the patient through a dialyzer separated by a semi-permeable membrane from a large volume of externally-supplied dialysis solution. The waste and toxins dialyze out of the blood through the semi-permeable membrane into the dialysis solution, which is then discarded.

The dialysis solutions or dialysates used during hemodialysis typically contain sodium chloride and other electrolytes (e.g., calcium chloride, or potassium chloride), a buffer substance (e.g., bicarbonate, or acetate and acid) to establish a physiological pH. Other substances can also be included in certain dialysates.

SUMMARY

Features of the methods and systems described herein can include the following. An example hemodialysis machine can include a door that separates a chamber of the hemodialysis machine from an outside environment. The chamber is part of a fluid circuit within the hemodialysis machine. A user can thus place salt into the chamber so that the hemodialysis machine can prepare the dialysis solution for use during dialysis treatment.

In one aspect, a hemodialysis machine includes a main body, a door connected to the main body, a fluid inlet and a fluid outlet, and a pumping mechanism. The door and the main body cooperate to define a non-removable chamber, and the door is openable relative to the main body of the hemodialysis machine to allow a salt to be placed into the non-removable chamber when the door is in an open position. The fluid inlet and the fluid outlet are in fluid communication with the non-removable chamber. The pumping mechanism is configured to deliver a fluid from a fluid source to the non-removable chamber through the fluid inlet to mix with salt within the non-removable chamber to form a salt solution that exits the non-removable chamber through the fluid outlet.

In some implementations, the fluid is purified water. The salt can be a powder. The salt can be a solution including dissolved salt.

In some cases, the door is placed into a closed position and a latched position and includes a handle that can be placed into an unlocked position and a locked position. Placing the handle into the locked position while the door is in the closed position can place the door into the latched position. The door can form a liquid-tight seal between the non-removable chamber and an outside environment when the door is in the latched position. The handle can be rotatable into the locked position and the unlocked position. The door can include a substantially translucent region.

In some examples, the non-removable chamber can be configured to receive a liner sized and dimensioned to be placed in fluid communication with the fluid inlet and the fluid outlet. The liner can define openings configured to receive the fluid inlet and the fluid outlet. The liner can be a multi-use disposable item. The liner can be configured to isolate walls of the non-removable chamber from the first fluid, the second fluid, and the salt. The non-removable chamber can include a sensor system that detects whether the non-removable chamber is sealed from the outside environment. The non-removable chamber can be a fluid reservoir In some examples, the fluid inlet is configured to receive the fluid at a first pressure and the non-removable chamber is configured to deliver the salt solution at a second pressure that is different than the first pressure.

In another aspect, a method of preparing a dialysis solution includes pouring salt into a non-removable chamber defined between a door and a main body of a hemodialysis machine and initiating a dialysis treatment during which a fluid mixes with the salt within the non-removable chamber to form a salt solution.

The method can further include, before pouring the salt into the non-removable chamber, placing a liner into the non-removable chamber of the hemodialysis machine such that initiating the dialysis treatment causes the fluid to enter the liner to form the salt solution. Pouring the salt into the non-removable chamber can include pouring the salt into the liner. Placing the liner into the non-removable chamber can further include forming a liquid-tight seal between the liner and the non-removable chamber. The method can include removing the liner from the non-removable chamber.

In some implementations, the method can further include initiating a cleaning operation of the hemodialysis machine during which a cleaning fluid rinses the non-removable chamber.

In some examples, pouring the salt into the non-removable chamber further includes opening the door covering the non-removable chamber, pouring the salt into the non-removable chamber through an opening defined by the open door and the hemodialysis machine, and closing the door. The door can include a substantially translucent region. The method can further include, after closing the door, latching the door to create a liquid-tight seal between the non-removable chamber and the outside environment. The door can include a handle, and latching the door can include actuating a handle such that the door compresses a gasket to form the liquid-tight seal. Actuating the handle can include rotating the handle.

In some cases, the salt is a powder. The non-removable chamber can be a fluid reservoir. The non-removable chamber can include a sensor system that detects whether the non-removable chamber is sealed from the outside environment.

Implementations can include one or more of the following advantages. The non-removable chamber reduces material use, environmental impact, and the cost associated with preparing a salt solution or dialysate for hemodialysis. Unlike hemodialysis performed with disposable containers of salt concentrate (e.g., sodium bicarbonate), the non-removable chamber can eliminate the manufacturing costs of these containers, the need for mechanical and fluid connections on the hemodialysis machine to directly interface with these containers, as well as the plastic waste produced by disposal of these containers. The chamber, its associated components, and containers to deposit the salt concentrate into the chamber are typically made of materials that allow them to be easily sterilized and reused for subsequent treatments.

In some implementations, the non-removable chamber can provide greater flexibility and efficiency for the user or operator. In selecting an amount of salt to include in the salt solution, rather than selecting from a limited number of pre-packaged containers having pre-determined specific amounts salt, the user can directly pour a desired amount of salt into the non-removable chamber. The non-removable chamber improves the efficiency of the cleaning process by allowing the user to clean the non-removable chamber as part of cleaning the fluid circuit of the hemodialysis machine. A user can simultaneously clean the hemodialysis machine and the non-removable chamber. Other aspects, features, and advantages will be apparent from the description and drawings, and from the claims.

DETAILED DESCRIPTION

Overview of Hemodialysis System

Figure 1:
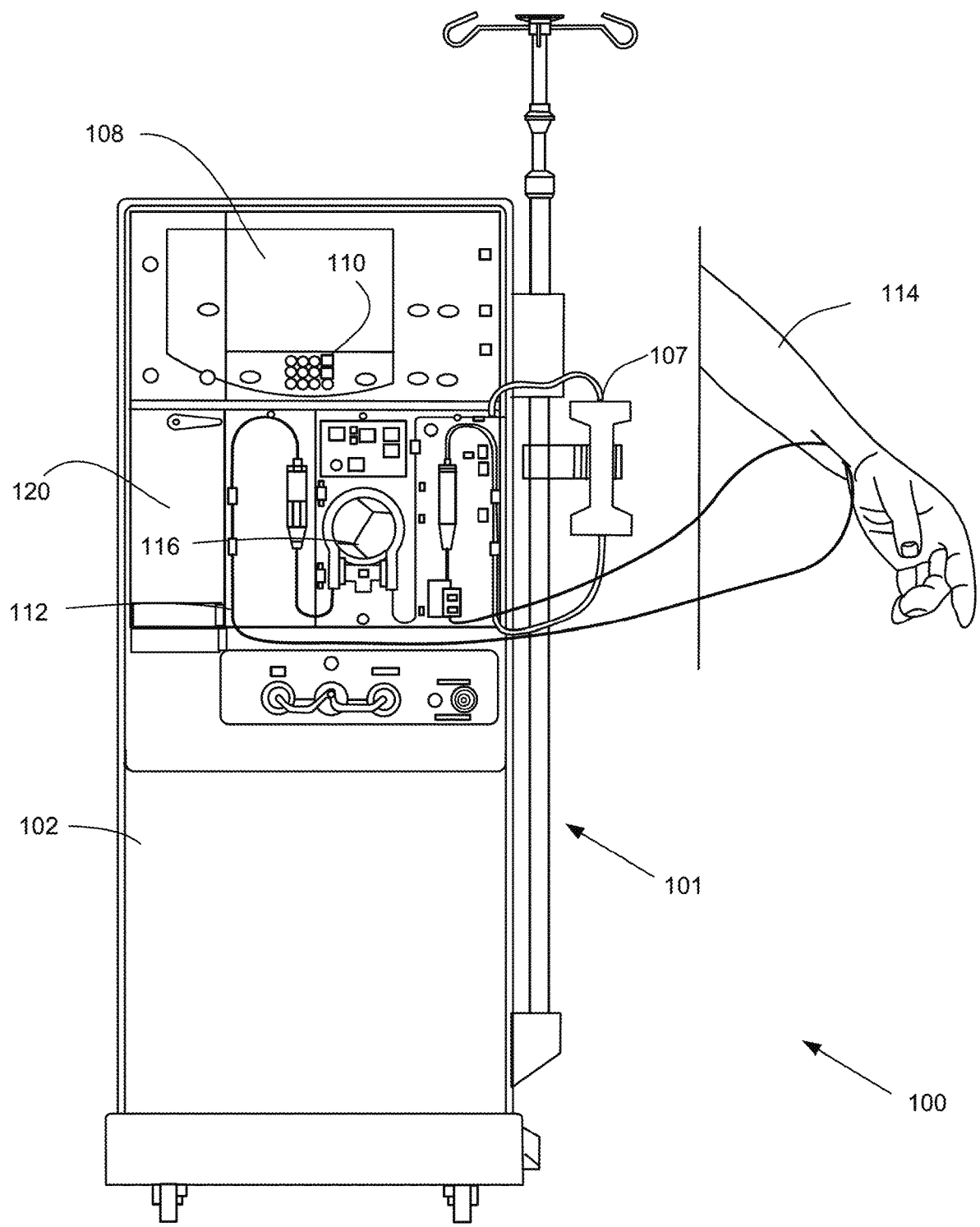
FIG. 1 depicts a hemodialysis system that is connected to a patient.

Referring to FIG. 1, a hemodialysis system 100 includes a hemodialysis machine 101. The hemodialysis machine 101 includes a main body 102 and a hydraulic system 104 (positioned mainly inside the hemodialysis machine 101 but schematically depicted in FIG. 4). The hydraulic system 104 prepares dialysate solution and conducts the solution to and from a dialyzer 107. The main body 102 of the hemodialysis machine 101 houses a touchscreen display 108 and a control panel 110 with which a user can interact to control treatment parameters.

Before the user initiates dialysis treatment, a disposable fluid line set 112 and the dialyzer 107 are connected to the hemodialysis machine 101 and to a patient 114. After the user initiates the dialysis treatment, a peristaltic pump 116 on the main body 102 circulates the patient's blood through the fluid line set 112 and the dialyzer 107. Dialysate fluid lines from the hydraulic system 104 also extend to the dialyzer 107 to allow dialysate to pass through the dialyzer 107 alongside the blood. A semi-permeable surface or membrane within the dialyzer 107 separates the blood and the dialysate. As the blood and the dialysate simultaneously pass through the dialyzer 107, toxins move from the blood across the semi-permeable membrane of the dialyzer 107 to the dialysate. The dialysate containing the toxins is hereby referred to as "spent dialysate."

As will be described in more detail later, the dialysate is prepared with a concentration of salts, a buffer, and fresh water. The dialysate properties, including the composition of salt, buffer, and fresh water, are typically tailored to the physiology of the patient 114. A buffer source, a reverse osmosis (RO) water source, and a salt source can deliver the substances to a dialysate preparation subsystem, which can then deliver the dialysate throughout the rest of the hydraulic system 104. A user can add salt to the dialysate preparation system by placing salt into the integrated salt solution compartment 120. As will also be described later, the integrated salt solution compartment 120 includes a chamber where the user can pour salt and where the salt and fluid solution can be mixed to form dialysate or a precursor to dialysate (e.g., a mixture of salt and RO water). The integrated salt solution compartment 120 is fixed to the main body 102 of the hemodialysis machine 101 and therefore cannot be removed from the hemodialysis machine 101. Preparation of the dialysate solution occurs in an integrated salt solution compartment 120 that reduces waste associated with using with conventional non-integral disposable containers of salt concentrate.

Integrated Salt Solution Compartment

Figure 2:
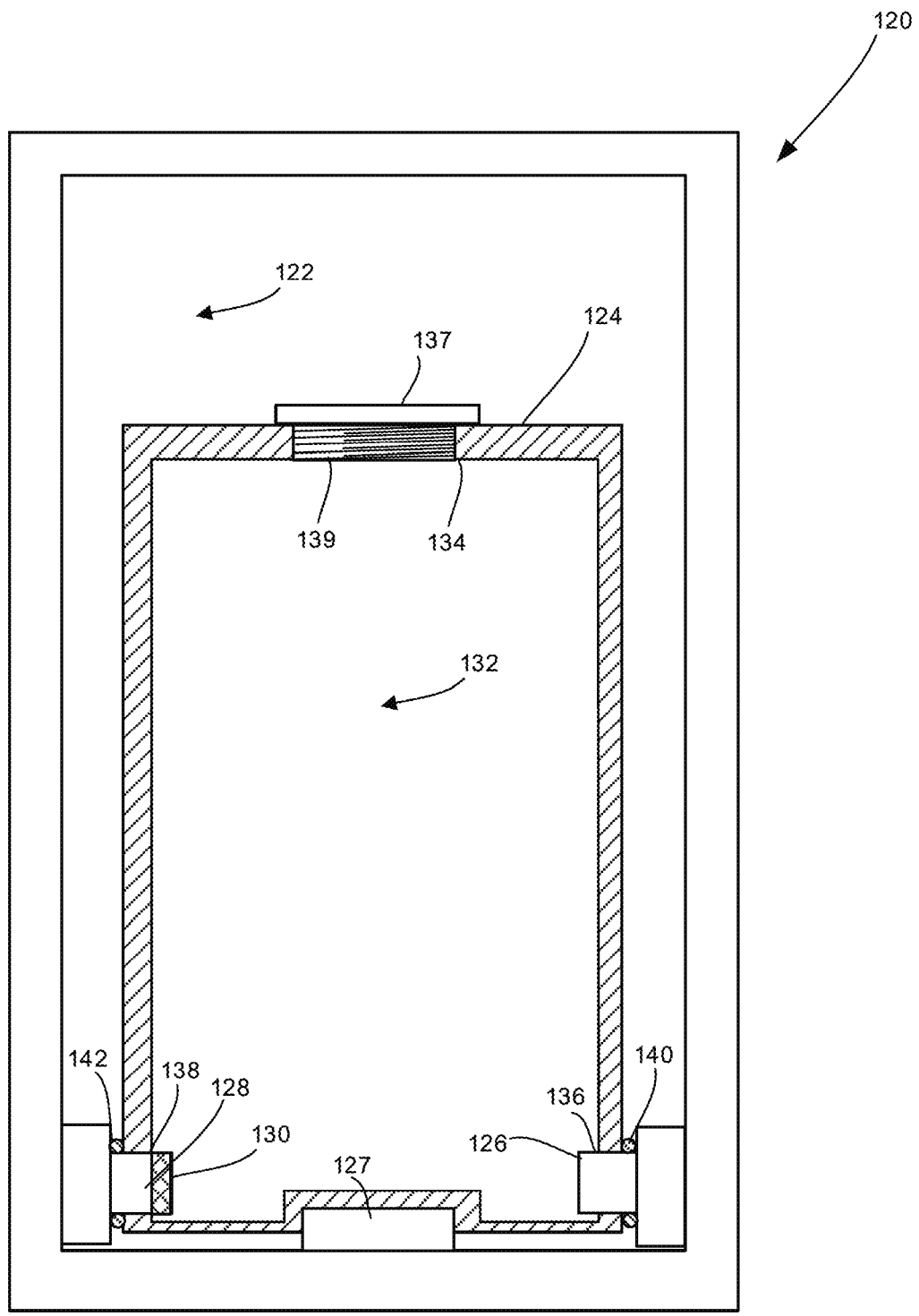
FIG. 2 is a front view of an integrated salt solution compartment of the hemodialysis system of FIG. 1.

FIG. 2 shows a front view of an integrated salt solution compartment 120 with a door of the compartment 120 removed. The integrated salt solution compartment 120 includes a compartment chamber 122, and a removable liner 124. The door (shown in FIGS. 3A-D), which can cover and uncover the compartment 120, is not shown in FIG. 2. As part of dialysis treatment, a user can deposit a powdered salt concentrate in the chamber 122 of the integrated salt solution compartment 120. The user can pour the salt concentrate from, for example, a disposable single-use container (e.g., a carton or a jug). The chamber 122 is part of a dialysate preparation subsystem of the hydraulic system 104 (described in more detail with respect to FIG. 4). In the chamber 122, the powdered salt concentrated is combined with a fluid (e.g., RO water) received from the hydraulic system 104. The fluid from the hydraulic system 104 enters the chamber 122 via a fluid inlet 126. The mixture of the salt concentrate and the fluid is conducted onward through a fluid outlet 128 to the hydraulic system 104, where the dialysate preparation subsystem can process the mixture and produce dialysate for delivery to the dialyzer 107 (shown in FIG. 1). The fluid inlet 126 and the fluid outlet 128 are disposed in a lower portion of the compartment chamber 122. The fluid inlet 126 and the fluid outlet 128 enter the compartment chamber 122 in a substantially horizontal orientation. As shown in FIG. 2, the fluid inlet 126 and the fluid outlet 128 are disposed on opposite sides of the compartment chamber 122. A filter 130 covers the fluid outlet 128 so that fluid delivered from the compartment chamber 122 into the hydraulic system 104 does not include large granules of undissolved solid salt concentrate.

Although the user has been described to deposit the powdered salt concentrate into the chamber 122, it should be understood that the user can deposit the salt within the chamber 122 without causing the salt to contact the walls of the chamber 122. In the example as shown in FIG. 2, the integrated salt solution compartment 120 includes the liner 124 that typically receives the salt poured by the user. During use of the integrated salt solution compartment 120 of FIG. 2, the compartment chamber 122 typically does not contact dialysis fluids and substances. A liner chamber 132 defined by the removable liner 124 thus receives and directly contacts the powdered salt concentrate and fluid. The liner 124 is placed into the compartment chamber 122 such that the bottom of the liner 124 aligns with an alignment boss 127, which limits side-to-side motion of the liner 124 when it is disposed in the compartment chamber 122. The liner 124 includes a threaded hole 134 through which a user can pour salt concentrate. The liner 124 includes holes 136 and 138 to accept the inlet 126 and the outlet 128, respectively. The inlet 126 inserts into the hole 136, and the outlet 128 inserts into the hole 138, thus placing the liner chamber 132 in fluid communication with the hydraulic system 104. Fluid entering through the inlet 126 is conducted into the liner chamber 132, and fluid exiting through the outlet 128 departs from the liner chamber 132. A removable cap 137 has a threaded portion 139 that mates with the threaded hole 134 of the liner 124. The removable cap 137 can thus be screwed onto the threaded hole 134 of the liner 124 such that the cap 137 and the liner 124 form a liquid-tight seal. The liquid-tight seal prevents fluid from escaping from the liner chamber 132 into the walls of the compartment chamber 122. The liner 124 and the removable cap 137 are typically made of a rigid polymer, such as polycarbonate (PC) or acrylonitrile butadiene styrene (ABS), and can be fabricated through an injection molding process.

Gaskets 140 and 142 surround the outer circumference of the inlet 126 and the outlet 128, respectively, to create a fluid-tight seal between the liner 124 and the inlet 126 and the outlet 128, respectively. The holes 136, 138 of the removable liner 124 are sized and dimensioned such that the liner 124 presses firmly against the gaskets 140, 142 when the liner 124 is placed on the inlet 126 and the outlet 128. The liner 124 typically compresses the gaskets 140, 142 enough to form a fluid-tight seal between the liner and the compartment chamber 122. The gaskets 140, 142 prevent fluid from leaking through the interface between the removable liner 124 and the inlet 126 and the outlet 128 into the compartment chamber 122.

Figure 3A:
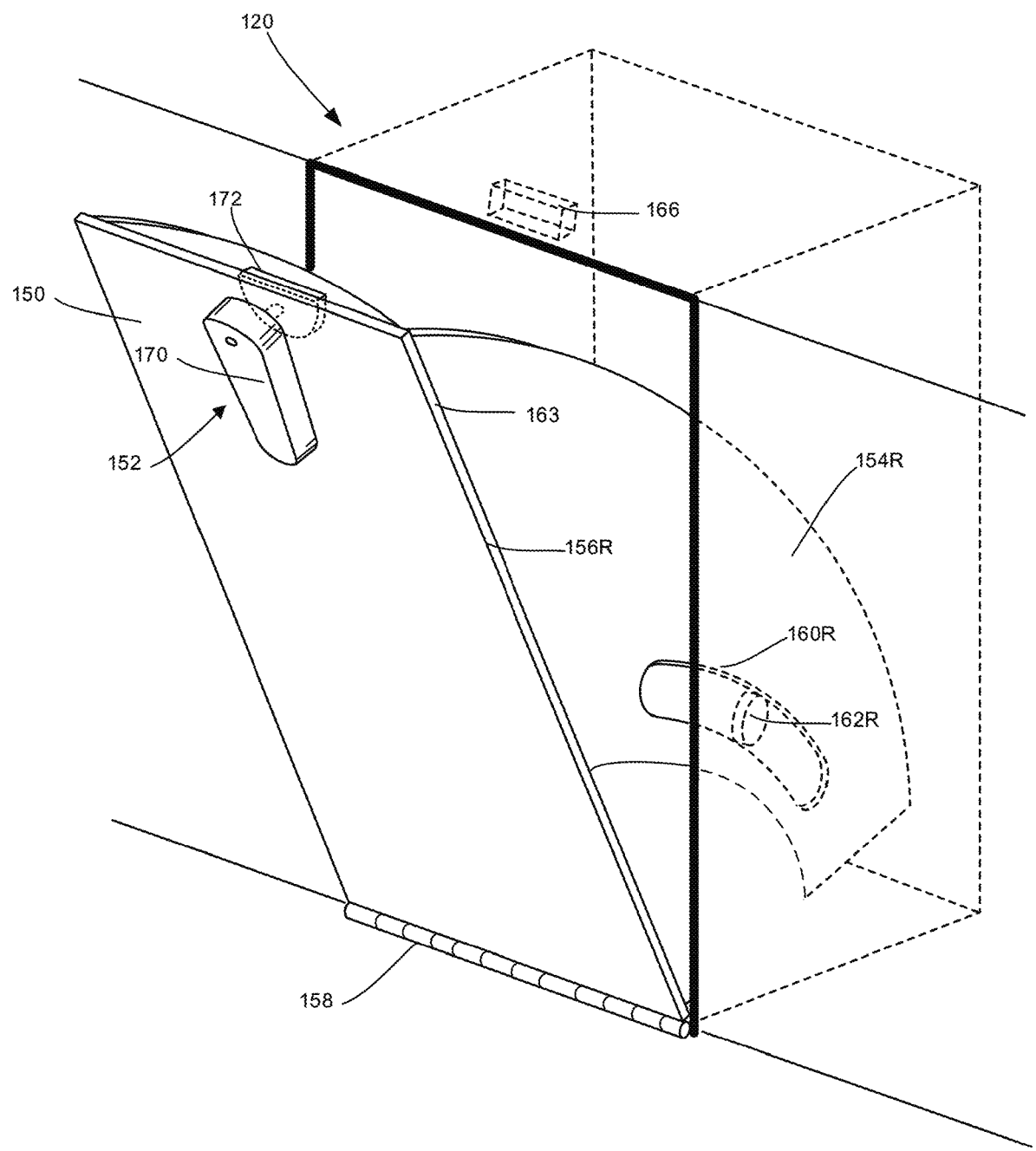
FIG. 3A-3D depicts perspective views of the integrated salt solution compartment of the hemodialysis system of FIG. 1. A door and a handle of the integrated salt solution compartment are in various positions.
Figure 3B:
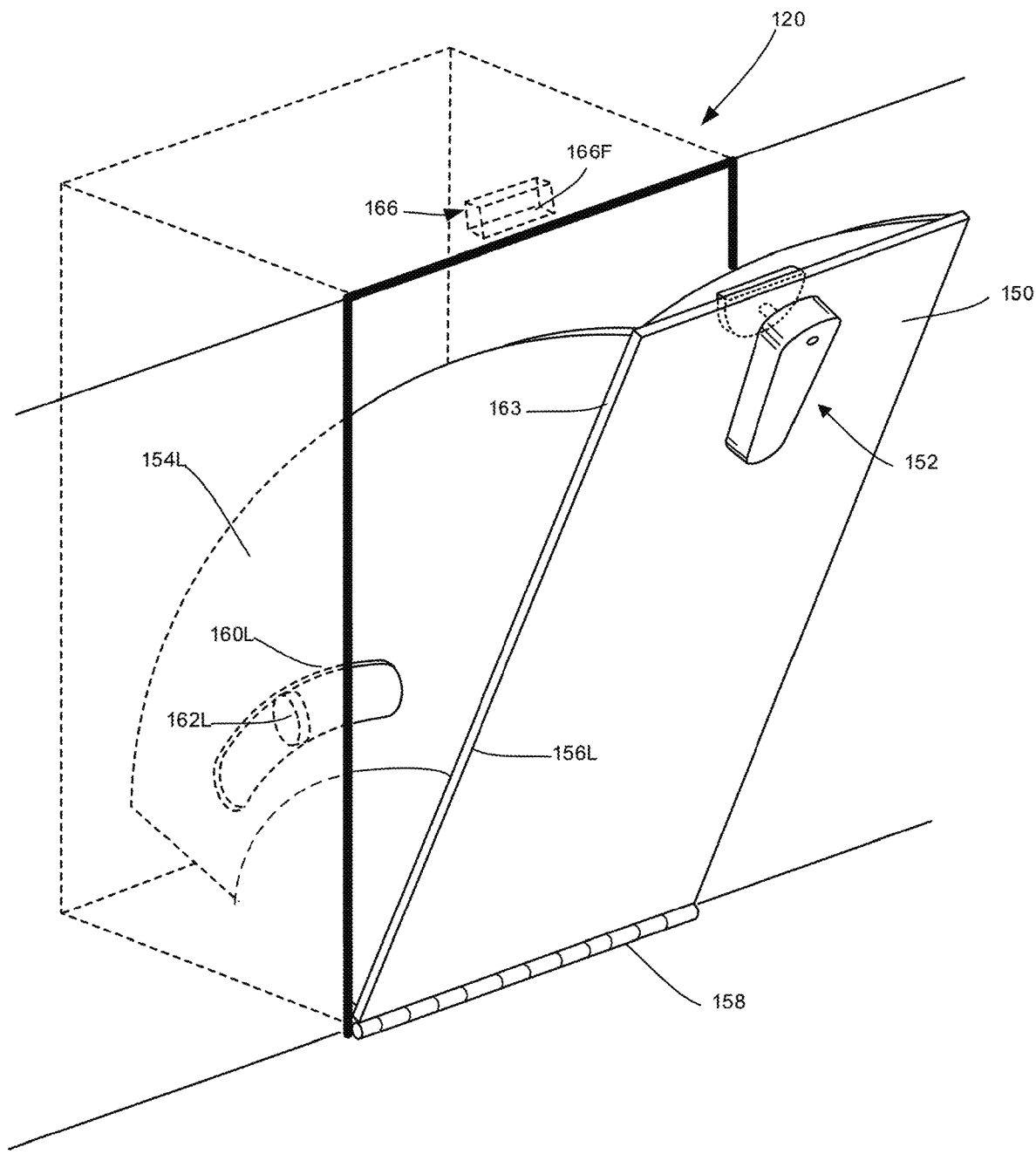
Figure 3C:
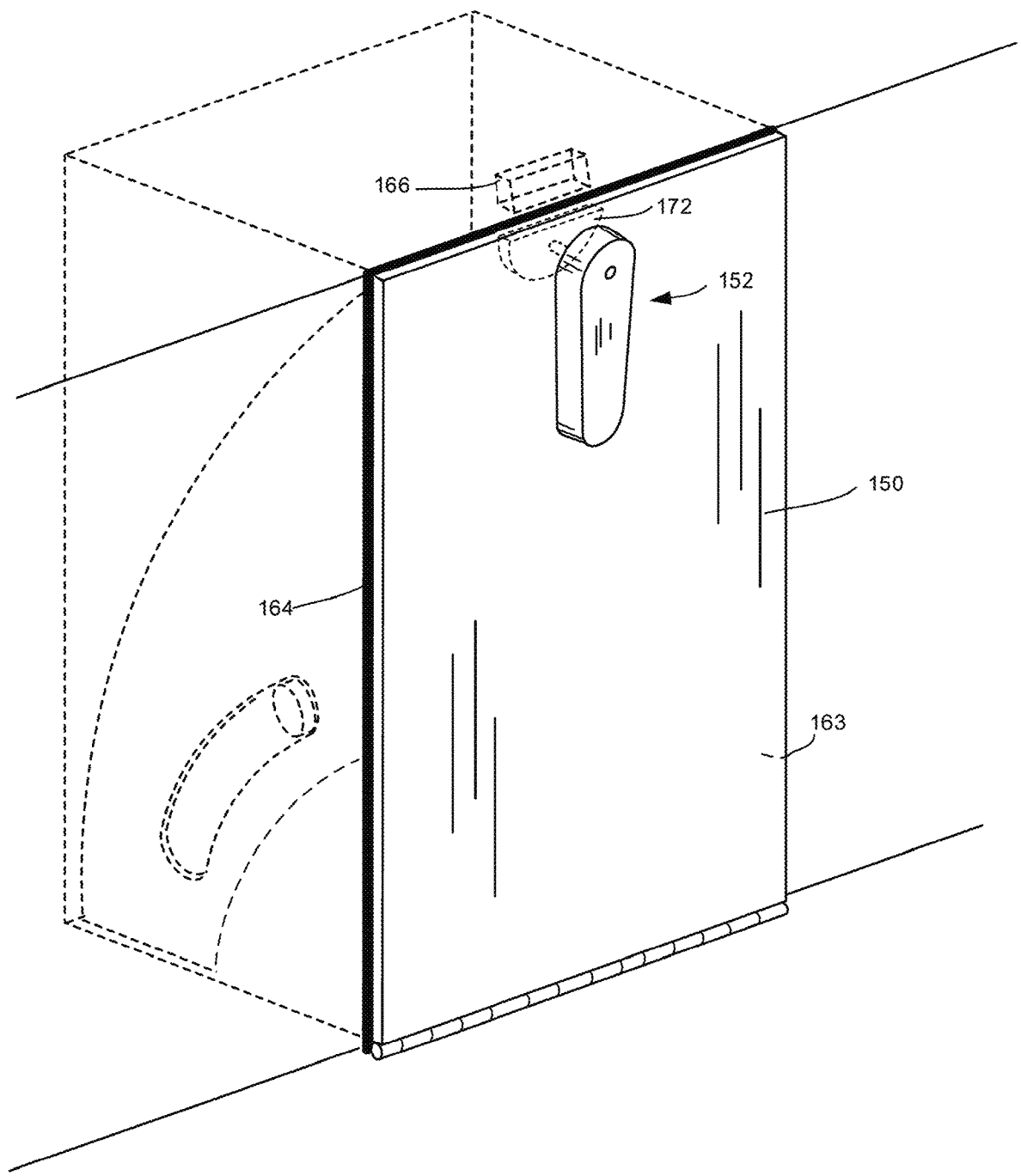
Figure 3D:
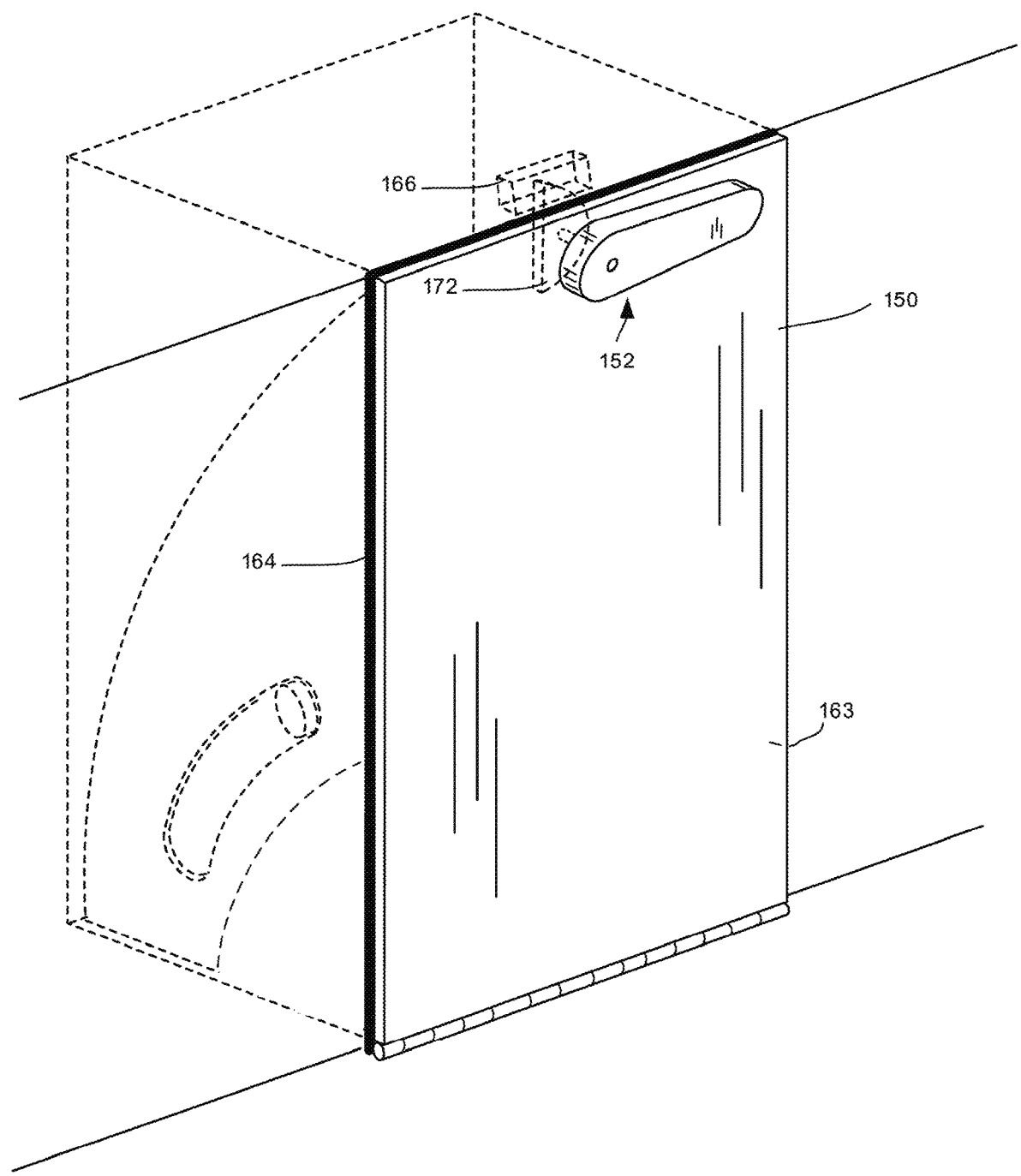

FIGS. 3A-D show an example of the integrated salt solution compartment 120 with the door 150 and the handle structure 152 in various positions. The door 150 can be placed in a fully open position (as depicted in the right and left perspective views of FIGS. 3A, 3B), a closed position (as depicted in FIG. 3C), and a latched position (as depicted in FIG. 3D). The handle structure 152 can be in an unlocked position (as shown in FIGS. 3A, 3B, and 3C) and a locked position (as shown in FIG. 3D).

Now referring to FIGS. 3A-B, the door 150 includes a left panel 154L and a right panel 154R. The door 150, the left panel 154L, and the right panel 154R are typically made of a flexible transparent material, such as polymethyl methacrylate (i.e., Plexiglas®), to allow a user to see operation of the integrated salt solution compartment 120. The panels 154L, 154R guide the rotation of the door, provide structural support, and ensure that solid salt concentrate powder or salt solution poured into the integrated salt solution compartment 120 flows into the compartment 120 and does not leak into the environment. The left and right panels 154L, 154R are fixed to the door 150 so that rotation of the door 150 results in a similar rotation of the panels 154L, 154R. The panels 154L, 154R are planar sheets that extend in a direction perpendicular to the door 150 into the hemodialysis machine 101. The left and right panels 154L, 154R extend through the length of the door 150 and are located about 0.25 inches from respective left and right edges 156L, 156R of the door. As will be discussed below, the left and right panels 154L, 154R and the left and right edges 156L, 156R outline an inside surface 163 of the door 150. The inside surface 163 assists in creating a fluid-tight seal between the compartment chamber 122 and an environment outside of the hemodialysis machine 101, as will be described in more detail below.

A hinge 158 attaches the door 150 to the hemodialysis machine 101. The hinge 158 is located on the outside of the hemodialysis machine 101 on a bottom portion of the door 150. The door 150 rotates about the hinge 158. The panels 154L, 154R rotate as the door 150 rotates about the hinge 158. Curved slots 160L, 160R on each panel 154L, 154R mate with guide pins 162L, 162R on the compartment chamber 122. The guide pins 162L, 162R travel along the curved slots 160L, 160R, respectively. The curved slots 160L, 160R limit the amount of rotation of the door 150 to a range of 45 degrees. The door 150 can be placed into three stable positions: the fully open position of FIGS. 3A-B, the closed position of FIG. 3C, and the latched position of FIG. 3D. The door 150 can be rotated into the closed position as shown in FIG. 3C. Referring to FIG. 3C, when the door 150 is placed in the closed position, the inside surface 163 of the door 150 contacts a gasket 164 on the hemodialysis machine 101 that surrounds the periphery of the integrated salt compartment chamber 122. The angular position of the door 150 at the closed position and the latched position depend on the configuration of a latching structure 166, which will be described below. The difference can be about 1 degree.

Referring back to FIG. 3A, a handle structure 152 traverses the door 150 and rotates about the center axis of a hole (not shown) of the door 150 where the handle structure 152 goes through the door 150. The handle structure 152 includes a handle 170 coupled with a latch 172, which is a flat semi-circular structure that engages a latching structure 166 on the hemodialysis machine 101 when the latch 172 is rotated into place. The latching structure 166 includes a sloped forward latching surface 166F. The forward latching surface 166F slopes such that the surface 166F increases in height (as measured from the bottom of the hemodialysis machine 101) the farther the surface 166F is into the hemodialysis machine 101. As the handle structure 152 rotates relative to the door, the latch 172 engages the latching structure 166 by contacting the forward latching surface 166F. As the latching structure 166 rotates, the slope of the forward latching surface 166F gradually pulls the door 150 into the hemodialysis machine 101. The door 150 includes two hard stops to limit rotation in both the counterclockwise and clockwise direction such that the handle structure 152 can rotate between about 0 and −90 degrees. At 0 degrees, the handle structure 152 is defined to be substantially horizontal with its free end pointing to the right. The handle structure 152 is in the locked position at 0 degrees, as shown in FIG. 3C. When the handle structure is in the locked position and door 150 is in the closed position, the latching structure 166 prevents the door 150 from being opened. At −90 degrees, the handle structure 152 is defined to be substantially vertical with its free end pointing toward the ground. The handle structure 152 is in the unlocked position at −90 degrees, as shown in FIG. 3A.

When the door 150 is in the closed position and the handle structure 152 is in the unlocked position as shown in FIG. 3C, the handle structure 152 can be rotated counterclockwise 90 degrees to be placed in the locked position as shown in FIG. 3D. Still referring to FIG. 3D, the rotation of the handle structure 152 rotates the latch 172, which then engages the latching structure 166 on the hemodialysis machine 101. Engagement of the latch 172 with the latching structure 166 causes the door 150 to be pulled toward the hemodialysis machine 101 to place the door 150 into the latched position shown in FIG. 3D. While the door 150 is in the latched position, the inside surface 163 of the door 150 compresses the gasket 164 to form a seal between the door 150 and the hemodialysis machine 101. To disengage the latch 172 from the latching structure 166 and to place the door 150 back into the closed position, the handle is rotated clockwise 90 degrees into the unlocked position shown in FIG. 3B. While in the closed position, as described above, the door 150 contacts the gasket 164 but does not necessarily form a fluid-tight seal. From the position in FIG. 3B, the handle structure 152 can be pulled to place the door 150 into the fully open position shown in FIG. 3A.

Hydraulic System of Hemodialysis Machine

Figure 4:
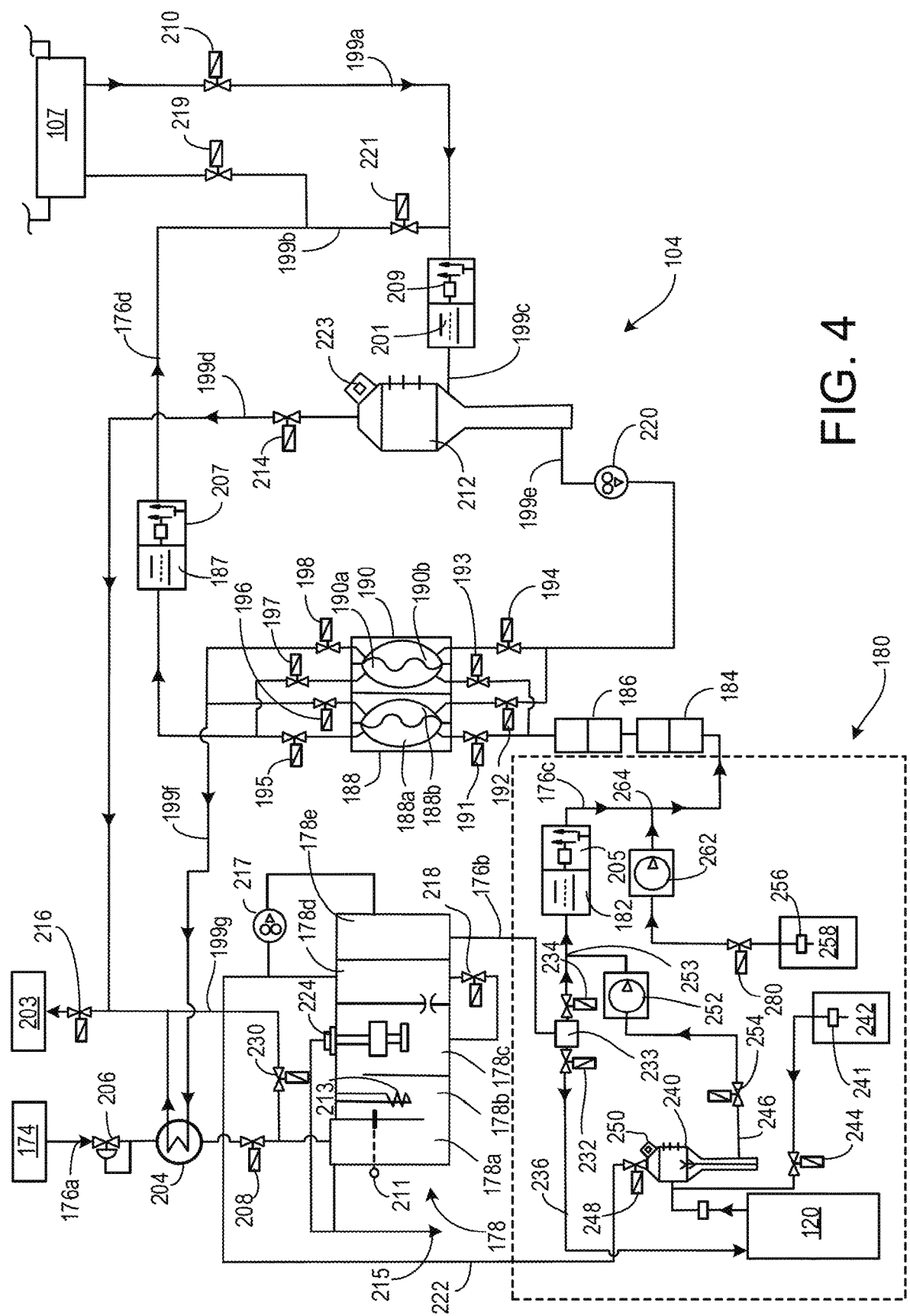
FIG. 4 is a schematic diagram of a dialysate circuit and associated components of the hemodialysis system of FIG. 1.

FIG. 4 shows the hydraulic system 104 of the hemodialysis machine 101 during treatment. Many of the illustrated components are housed inside the machine 101 and are thus not visible in FIG. 1. By way of a general overview of the hydraulic system 104 during treatment, fluid (e.g. purified water) enters the hemodialysis machine 101 from a fluid source 174. The hydraulic system 104 includes mainline segments 176a-d (collectively referred to as a mainline 176) that are fluidly coupled to chambers 178a-e (collectively referred to as a hydrochamber 178). Fluid exits the hydrochamber 178 and enters a dialysate preparation subsystem 180 of the hydraulic system 104. The subsystem 180 prepares a dialysate solution from the fluid, a salt concentrate, and a buffer. The subsystem 180 includes a conductivity detector 182, which is used to monitor the conductivity of a bicarbonate solution within the subsystem 180 to help ensure that the dialysate exiting the subsystem 180 has a desired bicarbonate concentration. Following the subsystem 180, the fresh dialysate is conducted through mixing chambers 184, 186 and balancing chambers 188, 190. Fresh dialysate passes through a conductivity detector 187 and enters the dialyzer 107 via the mainline 176. The conductivity detector 187 is used to ensure that the dialysate being delivered to the dialyzer 107 has a desired concentration of bicarbonate. The dialysate passes through the dialyzer 107 along with a patient's blood to filter the blood and remove toxins from the blood.

The machine 101 further includes return line segments 199a-g (collective referred to as a return line 199). Spent dialysate containing the removed toxins exits the dialyzer via the return line 199, along which a conductivity detector 201 is located, and enters the balancing chambers 188, 190. The conductivity detector 201 measures the conductivity of spent dialysate as it exits the dialyzer 107 to determine the effectiveness of dialysis treatment. The spent dialysate is sent from the balance chamber 188, 190 to a drain 203.

The conductivity detectors 182, 187, 201 are configured to measure conductivity of solutions at a specific temperature (e.g., 25 degrees Celsius). The temperature of the solution, however, varies as it is being raised to be passed through the dialyzer 107 to the patient. Therefore, the conductivity of the dialysate is determined by adjusting the signal received from each conductivity detector 182, 187, 201 based on the temperature of the solution as measured by temperature detectors 205, 207, 209 respectively. The amounts of adjustment are determined using equations that approximate temperature dependence of conductivity, such as the Steinhart-Hart equation. The temperature detectors 205, 207, 209 are typically thermistors, which are resistors in which the resistance varies significantly with temperature.

The hydraulic system 104 will now be described in greater detail. The fluid source 174 can provide an appropriate type of fluid or fluids, such as RO water. The fluid from the fluid source 174 flows through the mainline segment 176a to the hydrochamber 178. A heat exchanger 204, a pressure regulator valve 206, and a control valve 208 are provided along the mainline segment 176a between the fluid source 174 and the hydrochamber 178. The heat exchanger 204 transfers heat from spent dialysate heading toward the drain 203 to the fluid from the fluid source 174. The pressure regulator valve 206 is put into the closed configuration when the fluid pressure exceeds safe levels, and a shut-off valve 210 controls flow into the hydrochamber 178.

The hydrochamber 178 is a multichambered unit (chambers 12a-12e being illustrated) that serves several functions. The fluid temperature within the hydrochamber 178 is monitored and/or controlled by a control thermostat 211 disposed in the chamber 178a. A heater 213 in the chamber 178b heats the fluid based on the temperature measured by the control thermostat 211. In chamber 178c, air is vented to a venting structure 214 as the fluid flows through the various chambers 178a-e of the hydrochamber 178. A deaeration pump 217 pumps fluid between the chamber 178d and the chamber 178e to return the fluid to the mainline segment 176b.

To assist in the separation of gases from the fluid contained within the hydrochamber 178, the chamber 178c of the hydrochamber 178 includes a venting structure 224. Gases entering the chamber 178d from a degassing line 222 can go through a bypass valve 218 to reach the third chamber 178c, rise upward through the fluid contained within the hydrochamber 178 to the upper portion of the chamber 178c to be vented through the venting structure 224 to the atmosphere 215. The bypass valve 218 is typically a shut-off valve. Under normal operation, only gases are typically vented through the degassing line 222 to the hydrochamber 178. During cleaning modes of the machine, the valve 218 is opened in order to relieve pressure built up within the hydrochamber 178.

Leaving the hydrochamber 178, fluid enters the mainline segment 176b and flows into the subsystem 180 of the hydraulic system 104. The subsystem 180 prepares the dialysate solution, the process of which is discussed in further detail below. Referring briefly back to FIG. 2, a user adds salt (e.g., bicarbonate) to the subsystem 180 using the integrated salt solution compartment 120 as described above. The fluid enters the integrated salt solution compartment 120 through the fluid inlet 126, mixes with the salt poured by the user within the integrated salt solution compartment 120 (e.g., in the liner 124), and exits the compartment 120 through the fluid outlet 128. The fluid can enter the compartment 120 at a fluid pressure distinct from the fluid pressure of the fluid as it exits the compartment 120. The fluid containing salt and buffer leaves the subsystem 180 as dialysate and is directed to mixing chambers 184, 186, which mixes the dialysate to create a substantially homogeneous solution.

The dialysate continues to the balancing chambers 188, 190, through which flow is controlled by shut-off valves 191-198. Each of the balancing chambers 188, 190 includes two separate subchambers 188a-b and 190a-b, respectively. Subchambers 188a and 188b and subchambers 190a and 190b are each separated by flexible membranes.

Within the balancing chambers 188, 190, fresh dialysate from the subsystem 180 passes into one or both of subchambers 188*a*, 190*a* through the valves 191 and 193, respectively. The fresh dialysate fills the subchambers 188*a*, 190*a*, causing the flexible membranes to move into the adjacent subchamber 188*b*, 190*b*. As a result, spent dialysate, which was previously delivered to the subchamber 188*b*, 190*b* from the dialyzer 107, is expelled from the subchambers 188*b*, 190*b*. Subsequently, additional spent dialysate from the dialyzer 107 is pumped into the subchambers 188*b*, 190*b*, causing fresh dialysate to be expelled from the subchambers 188*a*, 190*a* and flow to the dialyzer 107. This process results in a balanced provision of fresh dialysate and spent dialysate from and to, respectively, the dialyzer 107 during use.

Leaving the subchambers 188*a* and 190*a* through the valves 195 and 197, respectively, the fresh dialysate is directed through the mainline segment 176*d*. The conductivity detector 187, which will be described in more detail later, measures the conductivity of the fresh dialysate flowing through the mainline segment 176*d*. A shut-off valve 219 in the mainline segment 176*d* and a bypass shut-off valve 221 in a bypass line 176*b* control fresh dialysate flow into the dialyzer 107. Dialysate flowing through the mainline segment 176*d* moves on to the dialyzer 107 when the valve 219 is in the open configuration and the bypass valve 221 is in the closed position. When the valve 219 is in the closed position and the bypass valve 221 is in the open position, fluid passes through the bypass line 176*b*. The fresh dialysate can, for example, be diverted through the bypass line 176*b* when the conductivity detector 187 detects a conductivity that is outside of an acceptable interval. This prevents incorrectly formulated dialysate from contacting the patient's blood within the dialyzer 107.

During treatment, both fresh dialysate and patient blood flows into the dialyzer 107. As a result, toxins, such as urea, are transferred across a semi-permeable structure (e.g., semi-permeable microtubes) of the dialyzer 107 from the patient's blood to the dialysate.

Following the dialyzer 107, spent dialysate (i.e. dialysate containing toxins) exits the dialyzer 107 and passes a shut-off valve 210 to return to the hydraulic system 104. The valve 210 controls spent dialysate flow out of the dialyzer into the return line segment 199*a*. When the control valve 210 is in the open position and the bypass valve 221 is in the closed position, spent dialysate flows into the return line segment 199*c*. The conductivity detector 201, which will be described in more detail later, measures the conductivity of the dialysate flowing through the return line segment 199*c*. The measurements of the conductivity detector 201 can, for example, be used in conjunction with the measurements of the conductivity detector 187 to determine the sodium concentration of the patient's blood and/or a clearance value associated with the treatment.

Spent dialysate passes into an air separation chamber 212 before reaching the balancing chambers 188, 190 to ensure accurate operation of the balancing chambers 188, 190. An air sensor 223 is provided in air separation chamber 212 to provide an indication of when a shut-off valve 214 should be opened to allow passage of gases from the air separation chamber 212 to the return line segment 199*d*. From the air separation chamber 212, separated gases, and potentially fluid, are passed through the return line segment 199*d* to the drain 203 by opening the valves 214 and 216. The air sensor 223 is a two-pronged air detection probe located at the top of the air separation chamber 212 such that an electric current between the two prongs is detected when dialysate fills the air separation chamber 212 to at least the level of the prongs. Conversely, when there is air in the air separation chamber 212, the air between the two prongs of the air sensor 223 acts as an insulator and electric current does not flow.

Spent dialysate, from which the gases have been separated in the air separation chamber 212, is pumped by a dialysate pump 220 through return line segment 199*e* to one or both of the subchambers 188*b*, 190*b* through the valves 192, 194, respectively. The dialysate pump 220 is a step pump. As described above, this causes fresh dialysate to be expelled from the subchambers 188*a*, 190*a*. Fresh dialysate is subsequently pumped into the subchambers 188*a*, 190*a* to expel the spent dialysate from the subchambers 188*b*, 190*b*. Leaving one or both of the subchambers 188*b*, 190*b* through the valves 196, 198, respectively, the spent dialysate flows through the return line segment 199*f* and is directed to the heat exchanger 204, where the spent dialysate typically transfers heat originally received from the patient blood when it pass through the dialyzer to the fresh dialysate. A bypass shut-off valve 230 and the valve 216 control the flow of fluid into the drain 203. When the bypass valve 230 is closed and the valve 216 is open, spent dialysate flows to the valve 216 into the drain 203. When the bypass valve 230 is open and the valve 216 is also open, fluid from the fluid source 174 flows directly into the drain 203 through the return line segment 199*g*.

The structure and operation of the subsystem 180 for preparation of the salt solution will now be explained in greater detail. Still referring to FIG. 4, the mainline segment 176*b* bifurcates at a junction 233. A shut-off valve 232 and a shut-off valve 234 control the flow of fluid to the mainline segment 176*c* and a subsystem line 236. If the valve 232 is closed and the valve 234 open, the fluid continues through the valve 234 to the mainline segment 176*c*. Conversely, if the valve 232 is open and the valve 234 closed, the fluid proceeds through the valve 232 to the subsystem line 236.

During treatment, fluid flowing through the mainline segment 176*b* from the hydrochamber 178 is directed to the subsystem 180 by opening the valve 232 and closing the valve 234 to provide flow to the subsystem line 236. To prepare a salt solution during treatment, fluid from the subsystem line 236 enters the integrated salt solution compartment 120 (as described in detail earlier), which contains a powdered salt concentrate. The integrated salt solution compartment 120 described earlier includes the removable liner that encloses the powdered salt concentrate, the inlet to receive the fluid from the subsystem line 236, and the outlet to deliver salt solution to the air separation chamber 240. The subsystem 180 further includes a salt solution port with a salt solution filter 241 that can be connected to a salt solution source 242. A shut-off valve 244 controls flow from the salt solution source 242. During treatment, the valve 244 is typically closed because the salt solution source 242 is not typically used.

In order to expel air from the subsystem 180, an air separation chamber 240 is provided within the subsystem 180. In order to determine when gas has accumulated in the air separation chamber 240, an air sensor 250 is provided in the air separation chamber 240. The air separation chamber 240, which is fluidly connected to the integrated salt solution compartment 120 by the subsystem line 236, is designed to remove both gases residually disposed within the salt solution compartment 120 and gases precipitating out of the salt solution during operation of the subsystem 180. During operation, air rises to the top of the air separation chamber 240, while the salt solution settles to the bottom of the air separation chamber 240. Salt solution is passed from the air separation chamber 240 to subsystem line 246, while gases are passed from the air separation chamber 240 to the degassing line 222 by operation of a shut-off valve 248. The air sensor 250 is a two-pronged air detection probe located at the top of the air separation chamber 240 such that an electric current between the two prongs is detected when dialysate fills the air separation chamber 240 to at least the level of the prongs. Conversely, when there is air in the air separation chamber 240, the air between the two prongs of the air sensor 250 acts as an insulator such that electric current does not flow between the two prongs.

Air flow through the air separation chamber 240 is controlled by the valve 248. If the air sensor 250 does not detect air in the air separation chamber 240, the valve 248 is closed, and the solution proceeds through subsystem line 246, advanced by a salt solution pump 252 to rejoin the mainline segment 176c at a junction 253. The salt solution pump 252 is a step pump. Conversely, if the air sensor 250 detects air in the air separation chamber 240, the valve 248 is opened to vent gases from the air separation chamber 240 to the degassing line 222. The degassing line 222 provides a fluid connection to the hydrochamber 178 such that gases accumulated in the air separation chamber 240 are passed to the hydrochamber 178. The degassing line 222 is connected to the chamber 178d of the hydrochamber 178. In use, only gases, rather than an air/salt combination, typically are released from the air separation chamber 240 through the valve 248, which is typically open for very short periods of time.

Turning first to the passage of salt solution from the air separation chamber 240, flow through the subsystem line 246 is controlled by operation of a shut-off valve 254. When the valve 254 is in the open position and the valve 248 is in the closed position, the salt solution flows through subsystem line 246 to the salt solution pump 252. The salt solution pump 252 pumps the salt solution to rejoin the mainline segment 176c at the junction 253. The salt solution passes through the conductivity detector 182 as it is conducted through the mainline segment 176c.

The subsystem 180 further includes a buffer port with a buffer filter 256 that can be connected to an acid concentrate solution container 258. A shut-off valve 260 controls flow from the buffer solution container 258. When the valve 260 is open, a buffer pump 262 pumps a buffer solution that rejoins the mainline segment 176c at junction 264. The buffer pump 262 is a step pump. The solution of fluid, salt, and buffer then exits the subsystem 180 as dialysate and is directed toward the mixing chambers 184, 186, then to one or both of the balancing chambers 188, 190, and on to the dialyzer 107 through the mainline segment 176d, as explained above.

As described above, the conductivity of the dialysate is measured at several points via the conductivity detectors 182, 187, 201. Disposed between the junction 253 and the junction 264, the conductivity detector 182 measures a value dependent on the conductivity of the mixture of fluid and salt solution. Disposed after the dialysate exits the balancing chamber 188, 190, conductivity detector 187 measures a value dependent on the conductivity of the solution of fluid, bicarbonate, and acid flowing into the dialyzer 107. Disposed after spent dialysate exits the dialyzer, conductivity detector 201 measures a value dependent on the conductivity of spent dialysate flowing from the dialyzer 107.

Methods of Use

A method of using the hemodialysis system 100 to administer a dialysis treatment to a patient 114 will now be described. Referring to FIGS. 1, 2, and 3A-3D, when the hemodialysis machine 101 is not in use, the door 150 of the hemodialysis machine 101 is typically in the latched position, and the handle structure 152 is in the locked position. Before treatment begins, an operator prepares the hydraulic system 104 to make dialysate by adding salt concentrate to the hydraulic system. The operator rotates the handle structure 152 clockwise into the unlocked position as shown in FIG. 3C. The operator then pulls open the door 150 into the fully open position as shown in FIG. 3B. While the door 150 is in this position, the operator places the removable liner 124 into the integrated salt solution compartment 120. The operator positions the liner 124 into the compartment 120 such that the inlet 126 and outlet 128 match with the holes 136 and 138, respectively. The operator also positions the liner 124 such that the liner mates with the alignment boss 127. The gaskets 140, 142 form seals between the liner 124 and the inlet 126 and between the liner 124 and the outlet 128, respectively. The operator then removes the cap 137 from the liner 124 to expose the liner chamber 132. The operator pours sodium bicarbonate powder into the liner chamber 132 through the hole 134.

After pouring a pre-determined amount of the sodium bicarbonate concentrate, the operator places the cap 137 on the removable liner 124 and grasps the handle structure 152 to push the door 150 back into the closed position as shown in FIG. 3B. The operator then rotates the handle structure 152 from the unlocked position into the locked position as shown in FIG. 3D. The handle structure 152 thus engages with the latching structure 166. The door 150 is subsequently in the latched position such that the gasket 164 forms a seal between the hemodialysis machine 101 and the inside surface 163 of the door 150.

Now referring to FIG. 1, before treatment begins, the operator enters treatment information into the hemodialysis machine 101 using the touchscreen display 108 or the control panel 110. The operator enters patient parameters and medical treatment information, and the hemodialysis machine 101 determines appropriate operating parameters for the patient's treatment. Once the patient parameters and the medical treatment information are entered, the operator prepares the fluid lines. The disposable fluid line set 112 is connected to the patient 114 and to the dialyzer 107, and the hydraulic system 104 is fluidly connected to the dialyzer 107.

The operator then initiates the hemodialysis treatment process. During hemodialysis, blood is circulated through the blood circuit (i.e., the various blood lines, the disposable fluid line set 112, and the dialyzer 107). At the same time, dialysate is circulated through the dialysate circuit (i.e., the various dialysate lines and dialysate components described with respect to the hydraulic system 104, including the dialyzer 107). Toxins are transferred from the blood to the dialysate, thus ridding the patient's blood of harmful substances.

When the hemodialysis treatment is complete, the operator disconnects and disposes the disposable fluid line set 112. The user unlocks the handle structure, opens the door, and removes the liner 124. The liner 124 and the removable cap 137 are cleaned and sterilized using a chemical sterilization process, such as an Ethylene Oxide (ETO) sterilization process. The liner 124 and the removable cap 137 can be reused for a subsequent hemodialysis treatment.

Alternative Implementations

In some cases, the integrated salt solution compartment is defined by the main body of the hemodialysis machine. The compartment is therefore non-removable and considered an integral aspect of the machine. In other implementations, the integrated salt solution compartment can be made of a rigid polymer distinct from the main body of the hemodialysis machine. The plastic compartment is non-removable and is fixed to the main body of the dialysis machine. The chamber within the integrated salt solution compartment is defined by the plastic compartment.

In some implementations, a top portion of the removable liner 124 includes a venting hole, which allows air within the liner chamber 132 to evacuate into the integrated salt solution compartment 120 as fluid displaces air in the liner chamber 132 during its delivery to the chamber 132. As the fluid enters and exits the liner chamber 132, the internal air pressure can remain relatively constant as air can easily flow into and out of the liner chamber 132 through the venting hole. The position of the venting hole along the top portion of the liner 124 in addition to the seals formed by the gaskets 140, 142 isolates the walls of the compartment chamber 122 from fluid during treatment.

While we have described the inlet 126 and outlet 128 to be disposed at a lower portion of the chamber 122, in some implementations, the inlet and outlet can be positioned in the upper portion of the chamber. A tube having a lower opening can be fluidly coupled to the outlet such that the opening is disposed in a lower portion of the chamber, that is, below the fluid level. Depending on the hemodialysis fluid circuitry, the inlet and outlets can also enter the compartment from an upper, lower, or lateral sides of the compartment. Similarly, a tube can also be attached the inlet.

While the curved slots 160R, 160L have been described to permit 0 to 45 degrees of rotation of the door 150, in other implementations, the interval of rotation can differ. For example, the upper limit of rotation can be smaller to reduce the possibility of salt concentrate from unintentionally escaping the liner chamber as the salt concentrate is poured into the liner chamber. In other implementations, the upper limit of rotation can be larger such that a larger liner can be easily placed into the integrated salt solution compartment.

A number of sensors can additionally be integrated into the integrated salt solution compartment 120. An optical sensor can be placed along an internal wall of the integrated salt solution compartment chamber to detect whether the removable liner has been placed in the compartment chamber. In other implementations, a force or pressure sensor can be placed along the gaskets for the inlet and the outlet. The sensor detects whether the removable liner has been securely placed on the inlet and the outlet. The integrated salt solution compartment can also include a fluid level sensor that determines the level of fluid within the removable liner. For example, if the removable liner is made of a transparent polymer, the fluid level sensor can be an optical sensor that senses the fluid level inside the removable liner during treatment. In other implementations, the sensor can measure the opacity of the fluid in the removable liner to determine, for example, the amount of salt concentrate dissolution. Other sensors that can be implemented into the integrated salt solution compartment can include weight sensors to determine the amount of fluid and/or concentrate within the integrated salt solution compartment, contact sensors to determine whether the door has been placed in the latched position, conductivity sensors to determine the concentration of salt of the fluid in the removable liner, etc. The compartment can include a scale that measures the amount of bicarbonate poured into the compartment. The sensor can deliver collected data to a controller on the hemodialysis machine that can further convey the information to an operator and/or activate alarms in response to abnormal data. Sensor data can be displayed on the touchscreen display of the hemodialysis machine.

While the liner 124 and the removable cap 137 have been described to be made of rigid polymeric materials through an injection molding process, in other implementations, other materials and processes are used. In some implementations, the removable liner is made from a blow molding process of a polymer. The removable liner can be fabricated from a transparent polymer resin so that a user can see into the liner. In other implementations, the removable liner is made of an elastomeric or low density polymer such as low density polyethylene or polyurethane. For these materials, the removable liner can be fabricated using a plastic film extrusion process such that the removable liner is deformable. The film can have sufficient thickness to withstand the fluid pressures and forces present in the liner during use. In other implementations, the liner 124 is made of a heat-resistant transparent material, such as borosilicate glass (commonly used in laboratory equipment).

While the venting hole 144 has been described simply to be a hole disposed at the top of removable liner 124, in some implementations, a hydrophobic semipermeable filter covers the venting hole. The filter ensures that only air—not fluid—escapes through the venting hole.

While the removable liner 124 has been described to include the venting hole 144, in some implementations, venting can occur through the removable cap 137. The threaded portion of the cap can mate with the threaded portion of the removable liner such that air can be vented through the threaded portions out of the removable liner. In other implementations, the cap can contain a venting hole that allows air to evacuate the removable liner.

While the door 150, the left panel 154L, and the right panel 154R have been described to be a transparent material such as Plexiglas® to allow the operator to view the inside of the integrated salt solution compartment, in other implementations, the door and panels can be of similar material to the chassis of the hemodialysis machine. It should be further understood that treatment can still be completed if the operator is unable to see the inside of the integrated salt solution compartment during treatment.

While the position of the panels 154L, 154R has been described to be about 0.25 inches from the left and right edges 156L, 156R of the door 150, other implementations can include a greater or lesser distance between the edges and the panels depending on, for example, the size of the gasket used to create the liquid-tight seal between the compartment and the door.

While the angular position of the door 150 at the closed position and the latched position has been described to differ by about 1 degree, in some implementations, the difference is smaller or greater. The difference can be greater when the gasket on the hemodialysis machine has a larger diameter so that the door can achieve a greater compression of the gasket. In implementations where the gasket is smaller, the difference in angular position is smaller. The slope of the forward surface of the latching structure can be adjusted accordingly to create a larger or smaller difference in angular position.

While we have described the mechanism to open and close the door 150 as being a hinge mechanism, the door can also be opened and closed through other kinematic mechanisms. For example, the door can be opened via a sliding mechanism where the door slides up and down along tracks disposed on the hemodialysis machine. In other implementations, the door can further include a smaller door or a drawer where the operator can pour salt concentrate without opening the door. For example, the small door or drawer can be configured such that salt concentrate poured through the small door or into the drawer will be delivered to the liner chamber. In further examples, the hemodialysis machine can include an orifice above the integrated salt solution compartment. The operator can pour salt solution or concentrate into the orifice, which is directly connected to the integrated salt solution compartment. The orifice directs the salt solution or concentrate into the liner chamber.

While we have described the door 150 and the machine 101 to engage via a rotatable latching mechanism facilitated by the handle structure 152, in other implementations, the engagement can occur by means of magnets, adhesives, or disengagable snap fits. For example, the inside surface of the door can be magnetically attractive to a surface on the hemodialysis machine. When the door comes in close proximity to the magnetic surface on the hemodialysis machine, the magnetic attraction generates sufficient force to compress the gasket enough to form a seal.

While we have described the door 150 as including a handle structure 152 that functions as part of the engagement mechanism between the door 150 and the machine 101, the handle structure 152 can be a static component. The door can include an additional actuation mechanism separate from the handle structure 152 that places the door in the latched position.

While we have described the removable liner 124 as a multi-use component, it can also be a single-use component.

While we have described the removable liner 124 to include the hole 134 and the cap 137 to serve as a fluid seal after the salt concentrate has been poured, the fluid seal can be formed through a sliding, rotating, or pivoting door or any other disengagable fluid seal known in the art.

While the removable liner 124 has been described as the receptacle for salt concentrate, in some implementations, the user can pour salt concentrate directly into the internal chamber of the integrated salt solution compartment. In between treatment, the internal chamber can be flushed with a cleaning solution such as hot water, a sodium hypochlorite solution, or an acid solution (e.g., acetic acid) to remove excess salt concentrate or deposits on the internal wall of the integrated salt solution compartment.

While the range of rotation that the curved slots 207a-b allows is described to be 45 degrees, in other implementations, the range is larger or smaller. For implementations where the removable liner is approximately the same size as the compartment chamber, a larger range allows a user to more easily remove or place the removable liner. In other implementations, the range is smaller such that the steepness of the door in the open position allows salt concentrate to easily flow down the surface of the door into the compartment chamber or the liner chamber.

While the operator has been described to pour sodium bicarbonate powder into the integrated salt solution compartment 120 prior to treatment, in some implementations, the user can pour a concentrated salt solution directly into the salt solution compartment. The hemodialysis machine can add additional purified water into the integrated salt solution compartment to dilute the solution. In other implementations, the operator pours salt concentrate directly into the liner prior to placing the liner into the integrated salt solution compartment. The inlet and the outlet of the integrated salt solution compartment can enter the removable liner through the top of the liner, as described in an alternative implementation above, so that the holes in the removable liner that accept the inlet and outlet are on the top portion of the removable liner. As a result, when an operator pours salt concentrate into the removable liner, the salt concentrate pools at the bottom of the liner.

While the liner 124 has been described to be cleaned and sterilized using a chemical sterilization process, in some implementations, the liner can be simply cleaned by initiating a fluid-based cleaning or disinfecting process of the hemodialysis machine 101. For example, during a disinfecting process of the hemodialysis machine, a disinfecting fluid, such as hot water or a sodium hypochlorite solution, can be circulated through the hydraulic system, including the integrated salt solution compartment. As the hydraulic system circulates the disinfecting fluid, the removable liner is cleaned and disinfected.

While a number of examples have been described for illustration purposes, the foregoing description is not intended to limit the scope of the implementations disclosed herein. There are and will be other examples and modifications within the scope of the following claims.

What is claimed is:

1. A method of preparing a dialysis solution, the method comprising:
   pouring salt into a chamber integral to a main body of a hemodialysis machine and defined between a door disposed on a lateral side of the main body and the main body of the hemodialysis machine; and
   initiating a dialysis treatment during which a fluid mixes with the salt within the chamber to form a salt solution.

2. The method of claim 1, further comprising:
   before pouring the salt into the chamber, placing a liner into the chamber of the hemodialysis machine such that initiating the dialysis treatment causes the fluid to enter the liner to form the salt solution,
   wherein pouring the salt into the chamber comprises pouring the salt into the liner.

3. The method of claim 2, wherein placing the liner into the chamber further comprises forming a liquid-tight seal between the liner and the chamber.

4. The method of claim 2, further comprising:
   removing the liner from the chamber.

5. The method of claim 1, further comprising:
   initiating a cleaning operation of the hemodialysis machine during which a cleaning fluid rinses the chamber.

6. The method of claim 1, wherein pouring the salt into the chamber further comprises:
   opening the door covering the chamber;
   pouring the salt into the chamber through an opening defined by the open door and the hemodialysis machine; and
   closing the door.

7. The method of claim 6, wherein the door comprises a substantially translucent region.

8. The method of claim 6, further comprising:
   after closing the door, latching the door to create a liquid-tight seal between the chamber and an outside environment.

9. The method of claim 8, wherein the door comprises a handle, and latching the door comprises actuating the handle such that the door compresses a gasket to form the liquid-tight seal.

10. The method of claim 9, wherein actuating the handle comprises rotating the handle.

11. The method of claim 1, wherein the salt is a powder.

12. The method of claim 1, wherein the chamber is a fluid reservoir.

13. The method of claim 1, wherein the chamber comprises a sensor system that detects whether the chamber is sealed from an outside environment.

14. The method of claim 1, further comprising moving the door relative to the lateral side of the main body of the hemodialysis machine into an open position to allow the salt to be poured into the chamber.

15. The method of claim 14, further comprising moving the door relative to the lateral side of the main body of the hemodialysis machine into a closed position before initiating the dialysis treatment.

16. The method of claim 14, wherein moving the door relative to the lateral side into the open position comprises rotating the door relative to the lateral side into the open position.

17. The method of claim 1, wherein initiating the dialysis treatment comprises:
    causing the fluid to be delivered into the chamber through a fluid inlet in communication with the chamber to form the salt solution, and
    delivering the salt solution through a fluid outlet in communication with the chamber.

18. The method of claim 1, wherein initiating the dialysis treatment comprises:
    causing a peristaltic pump to circulate blood from a patient through a disposable fluid line set.

19. The method of claim 1, wherein the door is positioned below a control panel housed by the main body, the control panel being operable to control treatment parameters for a hemodialysis treatment.

20. The method of claim 1, wherein initiating the dialysis treatment comprises causing a sensor positioned in the chamber to monitor a characteristic of the fluid within the chamber, the characteristic being selected from the group consisting of a fluid level of the fluid within the chamber and an opacity of the fluid within the chamber.

* * * * *